US005753615A

United States Patent [19]
Thorpe et al.

[11] Patent Number: 5,753,615
[45] Date of Patent: May 19, 1998

[54] NEUROPEPTIDES AND THEIR USE AS INSECTICIDES

[75] Inventors: Alan Thorpe; Hanne Duve, both of London, England; Anders Holten Johnsen, Copenhagen, Denmark; Stephen Tobe, Toronto, Canada

[73] Assignee: Queen Mary and Westfield College, London, England

[21] Appl. No.: 522,326

[22] PCT Filed: Mar. 14, 1994

[86] PCT No.: PCT/GB94/00507

§ 371 Date: Nov. 1, 1995

§ 102(e) Date: Nov. 1, 1995

[87] PCT Pub. No.: WO94/20530

PCT Pub. Date: Sep. 15, 1994

[30] Foreign Application Priority Data

Mar. 12, 1993 [GB] United Kingdom ............... 9305120

[51] Int. Cl.$^6$ ............... A01N 25/00; A01N 38/04; C07K 7/00; C07K 1/00
[52] U.S. Cl. .................. 514/2; 424/405; 514/13; 514/14; 514/16; 514/21; 530/326; 530/327; 530/328; 530/412
[58] Field of Search ................ 514/2, 12–19, 514/21; 424/405; 530/324–330, 412, 422, 417

[56] References Cited

U.S. PATENT DOCUMENTS 5,039,792 8/1991 Feyereisen et al. .

FOREIGN PATENT DOCUMENTS 0 421 935 4/1991 European Pat. Off. .

OTHER PUBLICATIONS

Donly, B.C., et al., "Molecular cloning of the gene for the allatostatin family of neuropeptides from the cockroach *Diploptera punctata*," *Proc. Natl. Acad. Sci. USA* 90:8807–8811 (Oct. 1993).

Duve, H., et al., "Isolation, structure, and activity of –Phe–Met–Arg–Phe–NH$_2$ neuropeptides (designated calliFMRFamides) from the blowfly *Calliphora vomitoria*," *Proc. Natl. Acad. Sci. USA* 89:2326–2330 (Mar. 1992).

Duve, H., et al., "Callatostatins: Neuropeptides from the blowfly *Calliphora vomitoria* with sequence homology to cockroach allatostatins." *Proc. Natl. Acad. Sci. USA* 90:2456–2460 (Mar. 1993).

Richard, D.S., et al., "Allatostatic regulation of juvenile hormone production in vitro by the ring gland of *Drosophila melanogaster*," *Molec. Cell. Endocrinol.* 68(2–3):153–161 (Jan. 22, 1990).

Woodhead, A.P., et al., "Primary structure of four allatostatins: Neuropeptide inhibitors of juvenile hormone synthesis," *Proc. Natl. Acad. Sci. USA* 86:5997–6001 (Aug. 1989).

Žitňan, D., et al., "Neurons Producing Specific Neuropeptides in the Central Nervous System of Normal and Pupariation–Delayed Drosophila," *Dev. Biol.* 156(1):117–135 (Mar. 1993).

*Primary Examiner*—Paula K. Hutzell
*Assistant Examiner*—Stephen Gucker

[57] ABSTRACT

This invention relates to novel neuropeptides isolated from *Calliphora vomitoria*, which are suitable for use in insecticidal formulations for controlling insects.

17 Claims, No Drawings

NEUROPEPTIDES AND THEIR USE AS INSECTICIDES

CROSS REFERENCE TO RELATED APPLICATIONS

This application is a U.S. national stage application under 35 U.S.C. § 371 of PCT International Application No. PCT/GB94/00507 filed on Mar. 14, 1994.

| (1) | Asp—Pro—Leu—Asn—Glu—Glu—Arg—Arg—Ala—Asn—Arg—Tyr—Gly—Phe—Gly—Leu—NH$_2$ (SEQ ID NO: 7) |
| (2) | Leu—Asn—Glu—Glu—Arg—Arg—Ala—Asn—Arg—Tyr—Gly—Phe—Gly—Leu—NH$_2$ (SEQ ID NO: 8) |
| (3) | Ala—Asn—Arg—Tyr—Gly—Phe—Gly—Leu—NH$_2$ (SEQ ID NO: 9) |
| (4) | (Asp)—Arg—Pro—Tyr—Ser—Phe—Gly—Leu—NH$_2$ (SEQ ID NO: 10) |
| or | (Asn) |

Neuropeptides capable of inhibiting the production of juvenile hormone by the corpus allatum of insects have been termed allatostatins. To date, members of this class of neuropeptides have been identified in only two species, from two different orders of insects. In the cockroach, *Diploptera punctata* (Order: Blattodea) five allatostatins ranging in size from 8 to 18 amino acids have been characterised. In the tobacco hornworm moth, *Manduca sexta* (Order: Lepidoptera) one allatostatin has been identified.

The References to these compounds together with their amino acid sequences are as follows:

(i) Woodhead A P, Stay B, Seidel S L, Khan M A and Tobe S S. (1989) Primary structure of four allatostatins: neuropeptide inhibitors of juvenile hormone synthesis. Proc. Natl. Acad. Sci. USA 86: 5997–6001 discloses the following sequences:

| 1. | Ala—Pro—Ser—Gly—Ala—Gln—Arg—Leu—Tyr—Gly—Phe—Gly—Leu—NH$_2$ (SEQ ID NO: 1) |
| 2. | Gly—Asp—Gly—Arg—Leu—Tyr—Ala—Phe—Gly—Leu—NH$_2$ (SEQ ID NO: 2) |
| 3. | Gly—Gly—Ser—Leu—Tyr—Ser—Phe—Gly—Leu—NH$_2$ (SEQ ID NO: 3) |
| 4. | Asp—Arg—Leu—Tyr—Ser—Phe—Gly—Leu—NH$_2$ (SEQ ID NO: 4) |

(ii) Pratt G E, Farnsworth D E, Fok K F, Seigel N R, McCormack A L, Shabanowitz J, Hunt D F, and Feyereisen R. (1991) Identity of a second type of allatostatin from cockroach brains: An octadecapeptide amide with a tyrosine-rich address. Proc. Natl. Acad. Sci. USA 88: 2412–2416 discloses the following sequence: Ala-Tyr-Ser-Tyr-Val-Ser-Glu-Tyr-Lys-Arg-Leu-Pro-Val-Tyr-Asn-Phe-Gly-Leu-NH$_2$ (SEQ ID NO:5); and (iii) Kramer S J, Toschi A, Miller C A, Kataoka H, Quistad G B, Li, J P, Carney R L, Schooley D A. (1991). Identification of an allatostatin from the tobacco hornworm *Manduca sexta*. Proc. Natl. Acad. Sci. USA 88: 9458–9462 discloses the amino acid sequence: pGlu-Val-Arg-Phe-Arg-Gln-Cys-Tyr-Phe-Asn-Pro-Ile-Ser-Cys-Phe-OH (SEQ ID NO:6)

The significance of these compounds lies in the fact that "in vitro" they have been shown to inhibit the production of juvenile hormone by the corpus allatum. This hormone plays a crucial role in insect development by controlling metamorphosis, adult sexual maturity and reproduction.

Interference with juvenile hormone biosynthesis and release through exploitation of the allatostatins could lead to insect control strategies that do not damage the environment.

The present invention is based on the discovery and potential practical commercial applications of one or more of five neuropeptides now identified from the blowfly,

*Calliphora vomitoria*. These are the first allatostatins to be isolated from insects belonging to the Order: Diptera.

The amino acid sequences of the newly discovered neuropeptides designated "callatostatins 1–4" are as follows:

The amino acid sequence of the more preferred neuropeptide termed "callatostatin 5" is:

(5) Gly-Pro-Pro-Tyr-Asp-Phe-Gly-Met-NH$_2$  (SEQ ID NO:11)

i.e. Glycine-Proline-Proline-Tyrosine-Aspartic Acid-Phenylalanine-Glycine-Methionine-Amide.

"Callatostatin 5," as defined above was isolated from extracts of whole flies. Subsequently, callatostatin 5 has been identified on three separate occasions from acid alcohol extracts of the separated heads of blowflies. Furthermore, it has been confirmed that the final methionyl residue is carboxyamidated by means of standard methylation procedures and comparisons of the masses of methylated and non-methylated peptides.

The extraction of the callatostatins from whole flies and also from separated heads was performed using 80% methanol/0.1M HCL/0.1% 2-mercapto-ethanol or a mixture of 87% methanol/5% acetic acid/8% water followed by acetone precipitation. Purification of the extracts was carried out by means of a series of HPLC step including the use of semipreparative (7.8 mm i.d.), analytical (3.9 mm) and narrow-bore (2.1 mm) columns using C18, C8, C4,Cyano and Phenyl and Waters Protein Pak 125 packing materials. Gradients of acetonitrile/water with 0.1% TFA or 10 mM ammonium acetate were used routinely. Schematically, this is shown in Table 1 below.

Function of Callatostatin 5.

This neuropeptide is the most potent inhibitor of juvenile hormone (JH) production so far known when tested in the "in vitro" bioassay using the corpora allata of the cockroach *Diploptera punctata*. Thus, it causes maximum inhibition of JH at a concentration of 1 nM, with a 50% inhibition (ED$_{50}$) being achieved at 0.1 nM. In comparison, the allatostatin of *Manduca sexta* has an ED$_{50}$ of 2 nM and the most potent of the naturally occurring allatostatins of *Diploptera punctata* has an ED$_{50}$ of 0.3 nM.

In experiments carried out on the blowfly itself, callatostatin appears not to act as an allatostatin. Thus, under the conditions of experiment we have so far applied we do not record an inhibition of juvenile hormone bisepoxide (JHB$_3$), the major JH compound in the blowfly.

Immunocytochemical studies have revealed that neurones containing this neuropeptide project not to the corpus allatum, (as they would if the peptide controlled JHB$_3$ production) but to integrative neuropil in the brain and thoracic ganglion and also to areas of the gut.

The 'essential novel features' of the five "callatostatins" compounds (1)–(5) above are as follows:

(i) They are the first of this group of compounds to be isolated from the major order of insects, the Diptera.

(ii) Callatostatin 5 has some similarities with the blattodean series of allatostatins (and is a homologue of the four other dipteran allatostatins (1) to (4)). However, this particular peptide is unique in having a C-terminal carboxyamidated methionyl residue. [The normal C-terminal pentapeptide motif of the allatostatins in both Diptera and Blattodea is -Tyr-Xaa-Phe-Gly-Leu-NH$_2$ (SEQ ID NO:17), where Xaa, in the peptides so far identified, is Gly, Ala, Ser, or Asn]. In callatostatin 5 Xaa is Asp, but unique to all the allatostatins, the terminal residue shows a substitution of methionine for leucine.

(iii) At the N-terminus, callatostatin 5 is unique, amongst all other allatostatins in having prolyl residues at positions 2 and 3. This pair of amino acids most probably confers conformational properties not possessed by any other of the allatostatins.

(iv) This naturally occurring blowfly neuropeptide is surprisingly and quite unexpectedly unique in having potent JH-inhibiting properties in another insect (the cockroach) in which it has not been shown to be present as a normal neuropeptide.

(v) The interspecific functionality described in (iv) is highly significant for potential insect control methods and formulations as explained by the following argument. Naturally occurring biologically active peptides (such as insulin in man) are present in exceptionally low concentration in the blood. To this end they are rapidly degraded by enzymatic processes within the body. Whilst normal, low levels of these active molecules have dramatic physiological effects, high blood titres are potentially damaging (hyperinsulinaemia, for example, may have fatal consequences).

(vi) Recent experiments suggest that one explanation for callatostatin 5's extremely potent JH-inhibiting properties in the cockroach may result from the inability of this species to degrade the blowfly peptide, perhaps due to its C— and N— terminal modifications.

The callatostatin neuropeptides (1) to (5) as defined above by amino acid sequence are embraced by the present invention in their substantially pure form and have commercially attractive potential as active insectidal agents. They inhibit reproduction or growth and development in cockroaches. These neuropeptides could well be an inhibitor of growth and development and/or reproduction in all other insect species.

In place of the extraction route from blowflies, the callatostatins (1) to (5), but (5) in particular could be synthesised from more conventional chemical routes, and techniques are known in the art for synthesising short chain peptide molecules, given the amino acid sequence. Accordingly it is within the competence of the notional skilled worker to make at least trial quantities of compounds (1) to (5) and particularly of the most preferred compound (5).

In one aspect of the invention we provide a "callatostatin" as herein defined as a compound, in substantially pure form, represented by the amino acid sequence defined above for callatostatins (1) to (5).

In another aspect of the present invention we provide insecticidal formulations which contain as active principle, one or more of callatostatins (1) to (5) as defined above. The insecticidal formulation may also comprise a carrier.

In a still further aspect of this invention we provide methods of controlling insects and killing insects, particularly of the order Blattodea, which comprise administering to the insects or to their immediate environment an insecticidal formulation which comprises one or more of callatostatins (1) to (5) as defined above. The insecticidal formulation may be administered as a spray. The method of controlling insects may comprise spraying an insecticidal formulation as defined above into an infested area. Preferably such formulations contain callatostatin (5) as herein defined as the major active principle.

We claim:

1. An isolated peptide which comprises an amino acid sequence selected from the group consisting of:

Asp Pro Leu Asn Glu Glu Arg Arg Ala Asn Arg Tyr Gly Phe
 1           5                   10
                                           Gly Leu  (SEQ ID NO:12),
                                            15

Leu Asn Glu Glu Arg Arg Ala Asn Arg Tyr Gly Phe
 1           5                   10
                                           Gly Leu  (SEQ ID NO:13),

Ala Asn Arg Tyr Gly Phe Gly Leu  (SEQ ID NO:14),
 1           5
Asx Arg Pro Tyr Ser Phe Gly Leu  (SEQ ID NO:15),
 1           5
Gly Pro Pro Tyr Asp Phe Gly Met  (SEQ ID NO:16).
 1           5

2. A peptide as claimed in claim 1, wherein said peptide further comprises a carboxy terminal residue which is carboxyamidated.

3. An insecticidal formulation comprising a peptide as claimed in claim 1 and a carrier.

4. A method of preparing an isolated peptide as claimed in claim 1, comprising:
   (i) extracting the peptide from either whole bodies or heads of *Calliphora vomitoria*;
   (ii) purifying the extracts using HPLC to obtain the peptide.

5. A method according to claim 4 wherein the peptide is extracted using methanol and either hydrochloric acid and mercaptoethanol, or acetic acid and water.

6. A method of preparing a peptide as claimed in claim 1, comprising chemically synthesizing said peptide.

7. A method of killing insects, comprising administering to the insects a peptide as claimed in claim 1.

8. A method of killing insects, comprising administering to the insects an insecticidal formulation as claimed in claim 3.

9. A method according to claim 8 wherein the insecticidal formulation is administered as a spray.

10. A method of controlling insects, comprising spraying an insecticidal formulation as claimed in claim 3 into an insect-infested area.

11. A method of controlling insects, comprising applying an insecticidal formulation as claimed in claim 3.

12. A method of controlling insects wherein death of said insects is caused by administering a peptide according to claim 1.

13. The method of claim 12, wherein said peptide further comprises a carboxy terminal residue which is carboxyamidated.

14. A method of inhibiting reproduction of an insect comprising administering to the insects a peptide as claimed in claim 1.

15. A method of inhibiting reproduction of an insect comprising applying an insecticidal formulation as claimed in claim 3.

16. A method of inhibiting growth and development of an insect comprising administering to the insects a peptide as claimed in claim 1.

17. A method of inhibiting growth and development of an insect comprising applying an insecticidal formulation as claimed in claim 3.

* * * * *

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Diploptera punctata ( i x ) FEATURE:
        ( A ) NAME/KEY: Modified-site
        ( B ) LOCATION:13
        ( D ) OTHER INFORMATION:/product="OTHER"
            / note= "C-terminal amide"

( x ) PUBLICATION INFORMATION:
        ( H ) DOCUMENT NUMBER: WO 94/20530 A2
        ( I ) FILING DATE: 14-MAR-1994

(J) PUBLICATION DATE: 15-SEP-1994

(x i) SEQUENCE DESCRIPTION: SEQ ID NO: 1:

```
Ala Pro Ser Gly Ala Gln Arg Leu Tyr Gly Phe Gly Leu
1               5                   10
```

(2) INFORMATION FOR SEQ ID NO: 2:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (v i) ORIGINAL SOURCE:
        (A) ORGANISM: Diploptera punctata (i x) FEATURE:
        (A) NAME/KEY: Modified-site
        (B) LOCATION:10
        (D) OTHER INFORMATION:/product="OTHER"
        / note= "C-terminal amide"

(x) PUBLICATION INFORMATION:
        (H) DOCUMENT NUMBER: WO 94/20530 A2
        (I) FILING DATE: 14-MAR-1994
        (J) PUBLICATION DATE: 15-SEP-1994

(x i) SEQUENCE DESCRIPTION: SEQ ID NO: 2:

```
Gly Asp Gly Arg Leu Tyr Ala Phe Gly Leu
1               5                   10
```

(2) INFORMATION FOR SEQ ID NO: 3:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (v i) ORIGINAL SOURCE:
        (A) ORGANISM: Diploptera punctata (i x) FEATURE:
        (A) NAME/KEY: Modified-site
        (B) LOCATION:9
        (D) OTHER INFORMATION:/product="OTHER"
        / note= "C-terminal amide"

(x) PUBLICATION INFORMATION:
        (H) DOCUMENT NUMBER: WO 94/20530 A2
        (I) FILING DATE: 14-MAR-1994
        (J) PUBLICATION DATE: 15-SEP-1994

(x i) SEQUENCE DESCRIPTION: SEQ ID NO: 3:

```
Gly Gly Ser Leu Tyr Ser Phe Gly Leu
1               5
```

(2) INFORMATION FOR SEQ ID NO: 4:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (v i) ORIGINAL SOURCE:
        (A) ORGANISM: Diploptera punctata ( i x ) FEATURE:
    ( A ) NAME/KEY: Modified-site
    ( B ) LOCATION:8
    ( D ) OTHER INFORMATION:/product="OTHER"
        / note= "C-terminal amide"

( x ) PUBLICATION INFORMATION:
    ( H ) DOCUMENT NUMBER: WO 94/20530 A2
    ( I ) FILING DATE: 14-MAR-1994
    ( J ) PUBLICATION DATE: 15-SEP-1994

( x i ) SEQUENCE DESCRIPTION: SEQ ID NO: 4:

Asp Arg Leu Tyr Ser Phe Gly Leu
1               5

( 2 ) INFORMATION FOR SEQ ID NO: 5:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Diploptera punctata ( i x ) FEATURE:
    ( A ) NAME/KEY: Modified-site
    ( B ) LOCATION:18
    ( D ) OTHER INFORMATION:/product="OTHER"
        / note= "C-terminal amide"

( x ) PUBLICATION INFORMATION:
    ( H ) DOCUMENT NUMBER: WO 94/20530 A2
    ( I ) FILING DATE: 14-MAR-1994
    ( J ) PUBLICATION DATE: 15-SEP-1994

( x i ) SEQUENCE DESCRIPTION: SEQ ID NO: 5:

Ala Tyr Ser Tyr Val Ser Glu Tyr Lys Arg Leu Pro Val Tyr Asn Phe
1               5                   10                  15

Gly Leu ( 2 ) INFORMATION FOR SEQ ID NO: 6:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Manduca sexta ( i x ) FEATURE:
    ( A ) NAME/KEY: Modified-site
    ( B ) LOCATION:1
    ( D ) OTHER INFORMATION:/product="OTHER"
        / note= "pyro-glutamic acid"

( x ) PUBLICATION INFORMATION:
    ( H ) DOCUMENT NUMBER: WO 94/20530 A2
    ( I ) FILING DATE: 14-MAR-1994
    ( J ) PUBLICATION DATE: 15-SEP-1994

( x i ) SEQUENCE DESCRIPTION: SEQ ID NO: 6:

Glu Val Arg Phe Arg Gln Cys Tyr Phe Asn Pro Ile Ser Cys Phe
1               5                   10                  15

( 2 ) INFORMATION FOR SEQ ID NO: 7:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Calliphora vomitoria ( i x ) FEATURE:
        ( A ) NAME/KEY: Modified-site
        ( B ) LOCATION:16
        ( D ) OTHER INFORMATION:/product="OTHER"
            / note= "C-terminal amide"

( x ) PUBLICATION INFORMATION:
        ( H ) DOCUMENT NUMBER: WO 94/20530 A2
        ( I ) FILING DATE: 14-MAR-1994
        ( J ) PUBLICATION DATE: 15-SEP-1994

( x i ) SEQUENCE DESCRIPTION: SEQ ID NO: 7:

```
Asp  Pro  Leu  Asn  Glu  Glu  Arg  Arg  Ala  Asn  Arg  Tyr  Gly  Phe  Gly  Leu
1                   5                        10                       15
```

( 2 ) INFORMATION FOR SEQ ID NO: 8:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Calliphora vomitoria ( i x ) FEATURE:
        ( A ) NAME/KEY: Modified-site
        ( B ) LOCATION:14
        ( D ) OTHER INFORMATION:/product="OTHER"
            / note= "C-terminal amide"

( x ) PUBLICATION INFORMATION:
        ( H ) DOCUMENT NUMBER: WO 94/20530 A2
        ( I ) FILING DATE: 14-MAR-1994
        ( J ) PUBLICATION DATE: 15-SEP-1994

( x i ) SEQUENCE DESCRIPTION: SEQ ID NO: 8:

```
Leu  Asn  Glu  Glu  Arg  Arg  Ala  Asn  Arg  Tyr  Gly  Phe  Gly  Leu
1                   5                        10
```

( 2 ) INFORMATION FOR SEQ ID NO: 9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Calliphora vomitoria ( i x ) FEATURE:
        ( A ) NAME/KEY: Modified-site
        ( B ) LOCATION:8
        ( D ) OTHER INFORMATION:/product="OTHER"
            / note= "C-terminal amide"

( x ) PUBLICATION INFORMATION:

(H) DOCUMENT NUMBER: WO 94/20530 A2
(I) FILING DATE: 14-MAR-1994
(J) PUBLICATION DATE: 15-SEP-1994

(xi) SEQUENCE DESCRIPTION: SEQ ID NO: 9:

```
Ala  Asn  Arg  Tyr  Gly  Phe  Gly  Leu
1                   5
```

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Calliphora vomitoria (ix) FEATURE:
        (A) NAME/KEY: Modified-site
        (B) LOCATION:8
        (D) OTHER INFORMATION:/product="OTHER"
        / note= "C-terminal amide"

(x) PUBLICATION INFORMATION:
        (H) DOCUMENT NUMBER: WO 94/20530 A2
        (I) FILING DATE: 14-MAR-1994
        (J) PUBLICATION DATE: 15-SEP-1994

(xi) SEQUENCE DESCRIPTION: SEQ ID NO: 10:

```
Asx  Arg  Pro  Tyr  Ser  Phe  Gly  Leu
1                   5
```

(2) INFORMATION FOR SEQ ID NO: 11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Calliphora vomitoria (ix) FEATURE:
        (A) NAME/KEY: Modified-site
        (B) LOCATION:8
        (D) OTHER INFORMATION:/product="OTHER"
        / note= "C-terminal amide"

(x) PUBLICATION INFORMATION:
        (H) DOCUMENT NUMBER: WO 94/20530 A2
        (I) FILING DATE: 14-MAR-1994
        (J) PUBLICATION DATE: 15-SEP-1994

(xi) SEQUENCE DESCRIPTION: SEQ ID NO: 11:

```
Gly  Pro  Pro  Tyr  Asp  Phe  Gly  Met
1                   5
```

(2) INFORMATION FOR SEQ ID NO: 12:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (x i) SEQUENCE DESCRIPTION: SEQ ID NO: 12:

Asp Pro Leu Asn Glu Glu Arg Arg Ala Asn Arg Tyr Gly Phe Gly Leu
1               5                   10                  15

(2) INFORMATION FOR SEQ ID NO: 13:

(i) SEQUENCE CHARACTERISTICS:
        (A) LENGTH: 14 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 13:

Leu Asn Glu Glu Arg Arg Ala Asn Arg Tyr Gly Phe Gly Leu
1               5                   10

(2) INFORMATION FOR SEQ ID NO: 14:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 14:

Ala Asn Arg Tyr Gly Phe Gly Leu
1               5

(2) INFORMATION FOR SEQ ID NO: 15:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 15:

Asx Arg Pro Tyr Ser Phe Gly Leu
1               5

(2) INFORMATION FOR SEQ ID NO: 16:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO: 16:

Gly Pro Pro Tyr Asp Phe Gly Met
1               5

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (i i) MOLECULE TYPE: peptide

```
( i x ) FEATURE:
    ( A ) NAME/KEY: Modified-site
    ( B ) LOCATION: 2
    ( D ) OTHER INFORMATION: /note= "Can be Gly, Ala, Ser, or
           Asn"

( i x ) FEATURE:
    ( A ) NAME/KEY: Modified-site
    ( B ) LOCATION: 5
    ( D ) OTHER INFORMATION: /note= "C-terminal amide"

( x i ) SEQUENCE DESCRIPTION: SEQ ID NO:17:

Trp  Xaa  Phe  Gly  Leu
 1              5
```